(12) United States Patent
Gerstenmeier (10) Patent No.: US 12,397,170 B2
(45) Date of Patent: Aug. 26, 2025

(54) DEVICE FOR ACTING ON AT LEAST PARTS OF A BODY

(71) Applicant: JK-HOLDING GMBH, Windhagen (DE)

(72) Inventor: Jürgen Gerstenmeier, Neuweid (DE)

(73) Assignee: JK-Holding GMBH, Windhagen (DE)

( * ) Notice: Subject to any disclaimer, the term of this patent is extended or adjusted under 35 U.S.C. 154(b) by 294 days.

(21) Appl. No.: 17/600,649

(22) PCT Filed: Apr. 2, 2020

(86) PCT No.: PCT/IB2020/053145
§ 371 (c)(1),
(2) Date: Oct. 1, 2021

(87) PCT Pub. No.: WO2020/202062
PCT Pub. Date: Oct. 8, 2020

(65) Prior Publication Data
US 2022/0161050 A1    May 26, 2022

(30) Foreign Application Priority Data
Apr. 3, 2019  (CH) .................................... 00455/19

(51) Int. Cl.
*A61N 5/06*     (2006.01)
(52) U.S. Cl.
CPC .... *A61N 5/0614* (2013.01); *A61N 2005/0615* (2013.01); *A61N 2005/0626* (2013.01);
(Continued)

(58) Field of Classification Search
CPC .......... A61N 5/0614; A61N 2005/0615; A61N 2005/0626; A61N 2005/0633;
(Continued)

(56) References Cited

U.S. PATENT DOCUMENTS 5,540,651 A  *  7/1996  Risch .................. A61H 9/0021
                                                    601/149
6,317,903 B1 * 11/2001  Brunelle ............... A61H 33/60
                                                    4/541.3
(Continued)

FOREIGN PATENT DOCUMENTS

CN       104423992 A    3/2015
CN       107958668 A    4/2018
(Continued)

*Primary Examiner* — Mark W. Bockelman
(74) *Attorney, Agent, or Firm* — HESLIN ROTHENBERG FARLEY & MESITI P.C.

(57) ABSTRACT

The invention relates to a device for acting on at least parts of the body of a user, in particular with medical-cosmetic radiation and/or by mechanical influence, comprising means for acting (22, 23) on the human body, which have adjustable operating parameters, and a controller (38), which is connected to the means for acting (22, 23) and sets the operating parameters. A device for acting on at least parts of the body of a user, which device can be set to the needs of the user, in particular even during operation, is provided according to the invention in that at least one microphone is provided, by means of which voice inputs of the user for controlling the operating parameters can be captured, and in that the microphone is connected to an evaluation unit, which converts voice inputs captured by the microphone into control commands for the means for acting (22, 23).

28 Claims, 2 Drawing Sheets

(52) U.S. Cl.
CPC ............... *A61N 2005/0633* (2013.01); *A61N 2005/0637* (2013.01); *A61N 2005/0652* (2013.01); *A61N 2005/0654* (2013.01); *A61N 2005/0655* (2013.01); *A61N 2005/0661* (2013.01); *A61N 2005/0663* (2013.01)

(58) Field of Classification Search
CPC .... A61N 2005/0637; A61N 2005/0652; A61N 2005/0654; A61N 2005/0655; A61N 2005/0661; A61N 2005/0663; A61N 2005/0651; A61N 5/0616; A61N 5/0618; A61B 2562/0271; A61B 2562/029; A61B 5/0022; A61B 5/4836; A61B 2017/00203; A61H 2039/005; A61H 2201/0207; A61H 9/0021; A61H 2201/10; A61H 2201/102; A61H 2201/1654; A61H 2201/5007; A61H 2009/0035; A61H 2201/5048; A61H 9/00; A61H 2203/0456; G06F 3/167; G10L 2015/223; G10L 15/02; A61M 21/02; A61M 21/0094

See application file for complete search history.

(56) References Cited

U.S. PATENT DOCUMENTS

| | | |
|---|---|---|
| 2003/0033666 A1 | 2/2003 | Hutsell |
| 2009/0031491 A1 | 2/2009 | Altman et al. |
| 2010/0088100 A1* | 4/2010 | Lindahl ............... G10L 15/1822 704/E15.04 |
| 2010/0191158 A1* | 7/2010 | Leventhal .......... A61H 23/0254 601/131 |
| 2013/0096473 A1 | 4/2013 | Berezhov |
| 2014/0316777 A1* | 10/2014 | Cha ..................... G06F 3/167 704/231 |
| 2014/0350411 A1 | 11/2014 | Gussen et al. |
| 2015/0174003 A2 | 6/2015 | O'Keefe et al. |
| 2016/0008568 A1 | 1/2016 | Attia et al. |
| 2016/0085317 A1* | 3/2016 | Agarwal ............... G06F 3/015 345/156 |
| 2017/0157431 A1 | 6/2017 | Cheatham, III et al. |
| 2017/0160710 A1* | 6/2017 | Kang .................. G05B 19/041 |
| 2017/0238401 A1 | 8/2017 | Sadwick et al. |
| 2017/0361125 A1 | 12/2017 | Lakios et al. |
| 2018/0014777 A1 | 1/2018 | Amir et al. |
| 2018/0172219 A1* | 6/2018 | Van Bommel ........... F21V 7/06 |
| 2018/0368762 A1 | 12/2018 | Pirtini Cetingul et al. |
| 2019/0019504 A1* | 1/2019 | Hatambeiki ............ G10L 15/20 |
| 2019/0019514 A1* | 1/2019 | Fava .................... A61F 9/00821 |

FOREIGN PATENT DOCUMENTS

| | | |
|---|---|---|
| CN | 108064007 A | 5/2018 |
| CN | 108743204 A | 6/2018 |
| CN | 108937932 A | 7/2018 |
| CN | 108969897 A | 12/2018 |
| DE | 4431402 C1 | 12/1995 |
| DE | 202007002980 U1 | 6/2007 |
| DE | 102010047188 A1 | 4/2012 |
| DE | 102012007504 A1 | 10/2013 |
| DE | 202018105021 | 9/2018 |
| EP | 1810713 A2 | 7/2007 |
| JP | H10508776 A | 9/1998 |
| JP | 2004526485 A | 9/2004 |
| JP | 2005000376 A | 1/2005 |
| JP | 2006345942 A | 12/2006 |
| JP | 2007520285 A | 7/2007 |

\* cited by examiner

Fig. 1

DEVICE FOR ACTING ON AT LEAST PARTS OF A BODY

This application is a national stage entry under 35 U.S.C. § 371 of International Application Number PCT/IB2020/053145, filed Apr. 2, 2020, and claims priority to Swiss application CH 00455/19, filed Apr. 3, 2019, the entire contents of which applications are hereby incorporated herein in their entireties.

The invention relates to a device for acting on at least parts of the body of a user, in particular with medical-cosmetic radiation and/or by mechanical influence.

Devices for acting on parts of a body are known from practice, in which the use of the eyes is not possible for regulatory reasons or for reasons of relaxation. For example, devices for acting on the body of a user by means of skin irradiation, in particular with ultraviolet light, are only to be used with protective glasses or at least with closed eyes, since the radiation can be harmful to the eyes in certain wavelengths. The known devices have the disadvantage of the circumstance that individual adaptations to desires or preferences of the user take place via a touch-sensitive display, which can hardly be seen with protective glasses.

In the field of irradiation of the skin, assemblies emitting medical-cosmetic radiation are used, the radiation of which produces a photobiological effect in an irradiated person. The medical-cosmetic radiation is incident here on the skin of the person, but depending on the specific wavelength can penetrate into deeper regions of the body. The effect comprises, for example, tanning of the skin, but also further physiological and psychological effects result from the irradiation. Medical-cosmetic radiation comprises the spectrum of ultraviolet (UV) radiation, visible (VIS) radiation, and near infrared (nIR) radiation. The UV radiation has wavelengths in the spectrum between 100 nm and approximately 380 nm in this case, the VIS radiation has wavelengths in the spectrum between approximately 380 nm and approximately 780 nm in this case, the nIR radiation has wavelengths in the spectrum between approximately 780 nm and 1400 nm in this case. The mentioned spectra merge into one another. Depending on the medical-cosmetic application, the radiation can be concentrated on a partial spectrum of the mentioned spectra. For this purpose, assemblies emitting medical-cosmetic radiation can also be associated with dedicated individual wavelengths, for example, the UV radiation which is generated by radiant tubes. However, the use of a radiant tube is not required. Due to the therapeutic effects of the medical-cosmetic radiation, it can also be referred to as medical-cosmetic-therapeutic radiation.

Devices for acting on the skin of a user are known from practice, as are used, for example, in tanning salons, in the case of which a person to be irradiated can lie on a cover forming a recumbent surface or finishing surface for the purpose of tanning their skin by pigmentation, wherein an assembly emitting UV radiation, generally having a plurality of radiant tubes, in particular fluorescent tubes, is arranged below the cover, wherein the cover can be removed or pivoted for the access to the radiant tubes. Such tanning devices usually also have a further module having further radiant tubes and a second cover, which can be pivoted jointly toward the person to be irradiated, so that the person can be tanned from two sides. It is problematic in this case that the user cannot readily adjust the operating parameters of the device during the irradiation without endangering his eyes or having to interrupt the operation.

So-called vertical sun beds are known from practice, in which the person to be irradiated does not lie horizontally on the cover, but rather is surrounded in the vertical position by the assembly emitting UV radiation. In a vertical sun bed, the radiant tubes extend in particular in the vertical direction.

It is the object of the invention to specify a device for acting on at least parts of a body of a user, using which a user can set the device to his requirements in particular also in running operation.

This object is achieved according to the invention by a device having the features of an independent claim.

According to one aspect of the invention, a device for acting on at least parts of a body of a user, in particular with medical-cosmetic radiation and/or by mechanical influence is provided, comprising means for acting on the human body which comprise adjustable operating parameters and a controller connected to the means for acting, which sets the operating parameters, which is distinguished in that at least one microphone is provided, by which speech inputs of the user for controlling the operating parameters can be captured, and the microphone is connected to an evaluation unit, which converts the speech inputs captured by the microphone into control commands for the means for acting. A possibility is advantageously provided in this way of setting one or multiple operating parameters of the device according to the wishes of the user with closed eyes, without the user having to use his eyes for this purpose, which is also advantageous in particular in the case of visually impaired persons. As a further advantage, the operating parameters can be set in running operation, so that the treatment which accompanies the acting on the parts of the body does not have to be interrupted, but rather is dynamically adaptable to the requirements of the user. The microphone provides an interface for the speech input, by way of which the user can make speech inputs, in particular in the form of commands, without opening the eyes for this purpose. The speech inputs captured by the microphone are associated with specific control commands in the evaluation unit which, if the control commands are clearly recognized, are output to the controller to set the means for acting accordingly.

It is obvious that speech inputs are possible not only during the operation of the device or during the duration of a specific application, but also before and/or after this. Thus, in particular the effect lighting of the device, generally colored LEDs in the visible light spectrum, can also be set, for example, by specifying the possible parameter variables color or brightness.

The evaluation unit expediently comprises a processor unit having a speech recognition unit, which analyzes the speech inputs captured by the microphone and transfers the control commands to the controller. The speech recognition unit is expediently equipped in this case with a number of terms stored in a memory unit of the speech recognition unit, which are assessed as a correct input upon exceeding a pre-settable degree of the correspondence of the speech input. Due to the provision of a local speech recognition unit in the device, it is not necessary to analyze the speech inputs on an external server and a rapid reaction to the speech inputs is possible. Furthermore, a high degree of error tolerance can be provided by the specification of a set of terms which are stored in the speech recognition unit.

A loudspeaker is preferably provided in the device, wherein the evaluation unit confirms successfully recognized speech inputs with an acoustic signal. According to a first embodiment variant, the acoustic signal can consist of the speech reproduction of the recognized control command, due to which in the case of an incorrect input the user recognizes this immediately and can counteract it by means of a new input. It is also possible to prompt questions to the user by means of a corresponding announcement, since the user can respond with yes or with no or with other clear specifications if the speech input could not be clearly assigned to a control command or if the correspondence to the stored speech data fell below a pre-settable threshold value. However, acknowledging the successful recognition of the speech input by an acoustic signal is particularly preferred, which communicates to the user that the speech input and the command linked thereto was recognized. The acoustic signal can also be combined with a tactile signal, for example a vibration.

The evaluation unit is expediently activatable by speech input of a keyword. The activation of the evaluation unit causes the subsequently captured speech inputs to be compared to terms stored in the evaluation unit in order to establish whether they are permissible control commands. This prevents the means for acting on the human body from being randomly changed due to discussions, noises from external sources, played back broadcast programs, or randomly used terms in the course of a conversation. The recognition of the keyword ensures here that the user intentionally wishes to perform a speech input and additionally prevents terms used which coincidentally correspond to control commands from resulting in incorrect changes of the operating parameters.

In a further advantageous embodiment, it is provided that the evaluation unit is activatable by touching a touch-sensitive display screen. A tactile interaction for activating the evaluation unit is thus possible, which then also enables the user to perform speech inputs if the keyword is not known or is not recognized by the evaluation unit. The touching of the display screen can also be acknowledged with an acoustic signal to signal the readiness to accept speech inputs to the user.

According to still a further preferred embodiment, it is provided that a separate button or a pushbutton is provided, wherein the evaluation unit is activatable by actuating the button. The button is expediently arranged next to the microphone, whereby speech inputs of a user are directed subconsciously in the direction of the microphone. It is alternatively also possible to position the corresponding button in the region of a hand rest surface for the user. Instead of a button, a touch-sensitive film or an electrical contact can also be provided, which is activatable by manual touch.

The device preferably has at least one display and at least one loudspeaker, whereby optical and/or acoustic explanations of the speech commands are displayable via the display and the loudspeaker. Thus, for example, at a time at which the user can still use his eyes, thus before the corresponding treatment, the possible speech inputs for control commands and the possible parameter variables for the speech inputs can be explained in written and acoustic form via an explanation video. This is advantageous in particular if users speaking a foreign language wish to control the device by means of speech input, who are not familiar with the statement of the terms used. In this way, the mode of operation of the device can advantageously also be explained at the same time and the adjustable parameters can be illustrated. One special advantage is that corresponding items of information can be updated upon the successive expansion of the speech input. At the same time, advertising films, items of information of the operator of the device, and the like can be emitted via the display.

In one particularly expedient refinement, the microphone of the device is connected to a control center external to the device and thus enables further inquiries with respect to the well-being of the user. Thus, for example, if the treatment lasts a long time, an operator of the control center can make contact with the user and make certain by his response that both the device and also the user are not subject to negative effects.

In a corresponding manner, the microphone of the device can be connected to a provider external to the device, for example via the Internet. The user can thus use the microphone even without generating his own control commands, for example, to telephone another person or to access content on the Internet. Outside the treatment, in addition optical contents from the Internet can also be displayed via the display provided in the device. A further or additional usage results in this way for the user, who can also use the microphone for the communication with external providers.

According to one particularly advantageous implementation, it is provided that upon capture of a speech input, in particular upon capture of the keyword or upon activation of the evaluation unit in another way, the operating parameters linked to a volume development are lowered or reduced by the controller. In this case, not only the operating parameters of the means for acting on the human body can be lowered, but also other operating parameters which are linked in particular to a noise development, for example, the playback of music and the like. Upon capture of a speech input, the operating parameters which develop noises are particularly preferably reduced, for example, the ventilation of the device in that the speed of the fan is reduced or the volume of music being played back, in that the music is either turned off entirely or its volume is reduced.

According to one particularly preferred embodiment, it is provided that acoustic signals played back via loudspeakers of the device are supplied via a separate input to the evaluation unit, and that they are inverted so that the noises captured randomly by the microphone are expressly not understood as a control command. It is thus possible, for example, upon playback of a speech, for example, a speech of a radio moderator, to neutralize this in the evaluation unit even if the program uses the keyword. In this way, it can be ensured in a particularly favorable manner that a random activation of the evaluation unit which could impair the experience of the acting is reliably prevented. The lowering of the operating parameter is preferably reversed a pre-settable time after end of an input, whereby it is signaled to the user that the evaluation unit is deactivated again.

The operating parameter which is to be set is expediently to be designated for the speech input, wherein the operating parameter is selected from a set of operating parameters which are stored in the evaluation unit. The corresponding operating parameter can be qualified by a parameter variable, so that the combination of operating parameter and parameter variable enables a simple and effective adjustment of the means for acting on the body. In addition, operating parameters which do not relate to the means for acting on the body can also be set, for example, the lighting or the temperature in the room in which the device is set up, or the volume of the music playback.

The operating parameters are expediently selected from the group comprising face lamps, body lamps, LEDs, body ventilation, face ventilation, temperature, moisture feed, music playback, volume, aroma feed, red light, blue light, waterjet strength, massage intensity, massage program, light program. It is not required for this purpose that the respective operating parameter designates the precise technical function. To set the intensity of the body ventilation, the speed of a corresponding pump is thus set without the pump having to be specifically designated for this purpose.

In addition to the operating parameters, a set of parameter variables can be predefined which characterize the operating parameters. In this case the parameter variable is expediently selected from the group comprising plus, minus, maximum, minimum, standard, on, off. The parameter variable "on" or "off" designates that the specific operating parameter is to be switched on or switched off, respectively. For example, light or music can be switched on or switched off in this way. However, it is also possible to switch the treatment as a whole on or off. The parameter variable "plus" and "minus" designates that in the case of scalable operating parameters the corresponding operating parameter is to be incremented or decremented. In this way, it is advantageously possible to raise or lower operating parameters divided into multiple levels without the specific number having to be selected or known for this purpose. In this way, it is advantageously made possible for the user to adapt operating parameters made too strong or too weak in the situation, without having to know the absolute value of the operating parameter for this purpose. In this way, in particular the user can advantageously adapt the operating parameters individually to his requirements during the treatment. The parameter variables "maximum", "minimum", and "standard" enable the user to set an operating parameter to the maximum, minimum, or standardized, generally moderate level without having to know for this purpose on which level the operating parameter is currently located. In this way, it is easily possible for the user to have the treatment carried out starting from a specific setting of the operating parameter.

It is furthermore possible to predefine specific designations of the means for acting using the speech input, by means of which a treatment is guided in the path. The speech input "massage on" can thus specify that a massage assembly is to be switched on to act on the body. The speech input "body ventilation plus" can thus specify that a body ventilation assembly for acting on the body is to be increased one level. The speech input "face lamps maximum" can thus specify that an assembly comprising face lamps for acting on the body, in the present case on the face of the user by means of medical-cosmetic radiation, is to be set to the maximum power.

It is possible to define further terms which are understood by the evaluation unit as commands which are not converted into control commands. For example, if the user effectuates the speech input "telephone", the evaluation unit can cause a mobile telephone which is coupled or can be coupled to the device to be provided for telephoning. The speech input "Internet", for example can cause the user to be able to access the Internet, in particular the speech input of his mobile terminal, for example a search engine.

The parts of the body on which the device acts are expediently selected from the group comprising the skin, the connective tissue, the musculature, and the bones. In particular in the case of the action on the body or its parts by means of mechanical influencing, the connective tissue and the musculature are regenerated, for example, by elastic deformation of the corresponding body parts. The perfusion of the body parts is stimulated and improved in this way and a regeneration effect is achieved. The transfer of the corresponding forces to the body or its parts can take place in a variety of ways, for example by pneumatic or hydraulic water jets which act directly on the body or indirectly via a membrane-like intermediate layer. The membrane-like intermediate layer can form a recumbent surface here on which the user can lay down. Other means for acting on the human body use radiation of different wavelengths, in particular ultraviolet radiation, visible radiation, and infrared radiation. The medical-cosmetic radiation acts on the outer skin layer, but also on regions of the body located underneath and in particular stimulates the pigmentation of the skin. In addition, parts of the body at different depths are reached as a function of the wavelength and the affected body part and thus are acted upon.

In one particularly advantageous embodiment, it is provided that specific speech parameters of the user are stored on a memory unit, for example on a customer card specific for the user. These specific speech parameters can be assessed by the evaluation unit after reading the data via an interface provided for this purpose to take into consideration specific pronunciations of the user in the evaluation of the captured speech inputs. In particular, an individual keyword which the user wishes to use can also be stored there. It is possible to store further items of information relating to the user on the memory unit, which enable it to greet the user by name or set his base setting for the device.

The controller expediently also sets means other than the means for acting on the human body, for example, the volume of music or the ambient temperature or the lighting, each outside the device.

According to one advantageous embodiment, it is provided that the device is designed as a hydromassage device having a membrane-like recumbent surface for the user, which has at least one activatable massage nozzle located underneath the recumbent surface, which can direct a massage waterjet against the membrane-like recumbent surface to massage the user lying thereon. It is obvious that multiple massage nozzles can be provided in coordination with one another for a symmetrical massage experience or independently from one another for simultaneously working different body regions.

According to another embodiment, it is provided that the means for acting are selected from the group comprising fluorescent tubes emitting UV light, fluorescent tubes emitting visible light, LEDs emitting UV light, LEDs emitting visible light, high-pressure lamps emitting UV light. The above-mentioned means are each designed to emit a predetermined partial spectrum of medical-cosmetic radiation which achieves, for example, a facial tanning or a tanning of the body. The different means can be set individually or in groups here.

According to one preferred refinement, it is provided that the microphone is designed as a microphone of a portable mobile terminal which is connectable in a wired or wireless manner to the device, due to which the installation of the microphone in the housing of the device is superfluous. The external microphone can capture speech inputs due to the connection to the evaluation unit. It is thus possible that the evaluation unit is also implemented on the portable mobile terminal, for example in a software application for the mobile terminal, because of which only the control commands then still have to be delivered from the mobile terminal to the control unit. However, the microphone is preferably installed in a housing of the device.

According to one aspect of the invention, a device is provided for acting on at least parts of a body of a user with medical-cosmetic radiation, comprising a self-supporting housing, in which an assembly emitting medical-cosmetic radiation for acting on the human body with adjustable operating parameters is housed, and a controller connected to the assembly for acting, which sets the operating parameters, wherein the device is distinguished in that at least one microphone is provided on the housing, by which speech inputs of the user for controlling the operating parameters can be captured, and that the microphone is connected to an evaluation unit, which converts the speech input captured by the microphone into control commands for the assembly for acting. In this way, a device designed in particular as a tanning device is advantageously provided, which can be controlled by speech inputs. In particular, the components of the assembly emitting medical-cosmetic radiation can be set by verbal input of control commands without the user having to make use of his eyes for this purpose, with the advantageous effect that the action of medical-cosmetic radiation, which is possibly harmful to the eyesight, on the visual organs is avoided. In addition, the user can concentrate on the remaining senses, which contributes to the relaxing effect. The user is no longer forced to interrupt the treatment for an adjustment of the operating parameters, whereby the degree of utility of the device is increased.

The means for acting are expediently housed in a self-supporting housing. It is thus advantageously ensured that the means for acting are reliably encapsulated and the means for acting are protected from dust and environmental influences.

The housing preferably comprises a stationary housing part and a movable housing part, wherein the movable housing part is coupled via a linkage axis to the stationary housing part. The movable housing part and the stationary housing part expediently form a vertical or a horizontal tube in this case, which does not have to have a cylindrical cross section, however. The housing parts are preferably formed as polymethyl methacrylate at least predominantly transparent for medical-cosmetic radiation, which is also referred to as acrylic glass, through which the radiation can pass with low losses.

The housing expediently comprises a stationary housing part and a movable housing part, wherein the movable housing part is coupled via a linkage axis to the stationary housing part. In this way, the housing can advantageously be pivoted up for the access of the user and can be closed before the action on the user.

In one advantageous refinement, it is provided that the stationary housing part forms a recumbent surface for the user, which is predominantly planar. The movable housing part is then pivotable down to the stationary housing part to form a tube. The possibility is advantageously provided in this way that the user can take a space recumbent in the device, namely with the back on the recumbent surface.

A microphone is expediently arranged on the movable housing part, so that the user lying with his back on the recumbent surface is facing toward the microphone with his face. The microphone can capture the soundwaves originating from the user well in this way.

According to one preferred embodiment, the microphone is arranged at one axial end of the movable housing part. It is particularly advantageously ensured in this way that the wires which are required for the contacting of the microphone cannot be seen through the acrylic glass by the user. In addition, the microphone is thus arranged outside the essential regions of the radiation and the risk that the metallic components of the microphone will heat up is thus reduced. The microphone is expediently arranged at an axial head end of the movable housing part.

According to one preferred embodiment, it is provided that the microphone is arranged in a drilled hole of in a stable plastic shell which forms the housing part and is at least predominantly transparent for medical-cosmetic radiation. The drilled hole ensures that the soundwaves originating from the user are reliably captured.

The microphone is expediently arranged outside the region of the direct action of the medical-cosmetic radiation, so that neither aging effects due to the UV light nor temperature-induced effects occur on the microphone.

The microphone is expediently arranged in the region of a frame section of the housing reinforcing the housing part, in particular the movable housing part, due to which the terminal of the microphone may be concealed in a visually advantageous manner.

According to one aspect of the invention, a method for acting on at least parts of a body of a user, in particular with cosmetic-medical radiation and/or by mechanical influencing, comprising means for acting on the human body which comprise adjustable operating parameters, and a controller connected to the means for acting which sets the operating parameters, in which the user specifies at least some of the operating parameters by speech input, and in which the speech inputs captured by at least one microphone are converted by an evaluation unit into control commands for the means for acting. In this way, the user, who cannot or is not permitted to use his eyes—this is the rule in devices for acting on the skin by means of UV radiation—can advantageously perform changes of settings of the device for acting, in particular the means for acting, even in running operation, whereby the well-being of the user and his trust in the product are increased.

The method can also be used in particular as a method for operating the device, in particular the device described above, so that a method for operating a device for acting results, which has the features of the above-mentioned method.

The evaluation unit is preferably activated by speech input of a keyword, and the speech inputs following the speech input of the keyword are compared in the evaluation unit for correspondence with stored commands for operating parameters. In this way, inadvertent mentions of individual control commands are advantageously only considered if the evaluation unit was previously put into a state of actively capturing the speech inputs by the mention of the keyword. Inadvertent incorrect operations are avoided in this way.

In one advantageous refinement, it is provided that the operating parameters stored in the evaluation unit are selected from the group comprising face lamps, body lamps, LEDs, body ventilation, face ventilation, temperature, moisture feed, music playback, volume, aroma feed, red light, blue light, waterjet strength, massage intensity, massage program, light program.

The operating parameters are expediently qualified by parameters which are also detectable by means of speech input. Parameter variables are preferably stored in the evaluation unit for the stored operating parameters, which are selected from the group comprising plus, minus, maximum, minimum, standard, on, off.

An improved identification of the speech input results if upon capture of a speech input, operating parameters connected to a volume development are lowered by the controller, and that the lowering is reversed a pre-settable time after the end of an input. For this purpose, the speech input of a keyword, for example a first name or a last name, for example Eve, Aphrodite, Hera, or Venus, can advantageously be provided for activating the evaluation unit.

It is obvious that the method can also be refined by the features set forth above in conjunction with the devices. In particular, the method is executable on a correspondingly designed device.

Further advantages, features, properties, and refinements of the invention result from the following description of a preferred exemplary embodiment and from the dependent claims.

The invention is explained in more detail hereinafter with reference to the appended drawings on the basis of a preferred exemplary embodiment.

Figure 1:
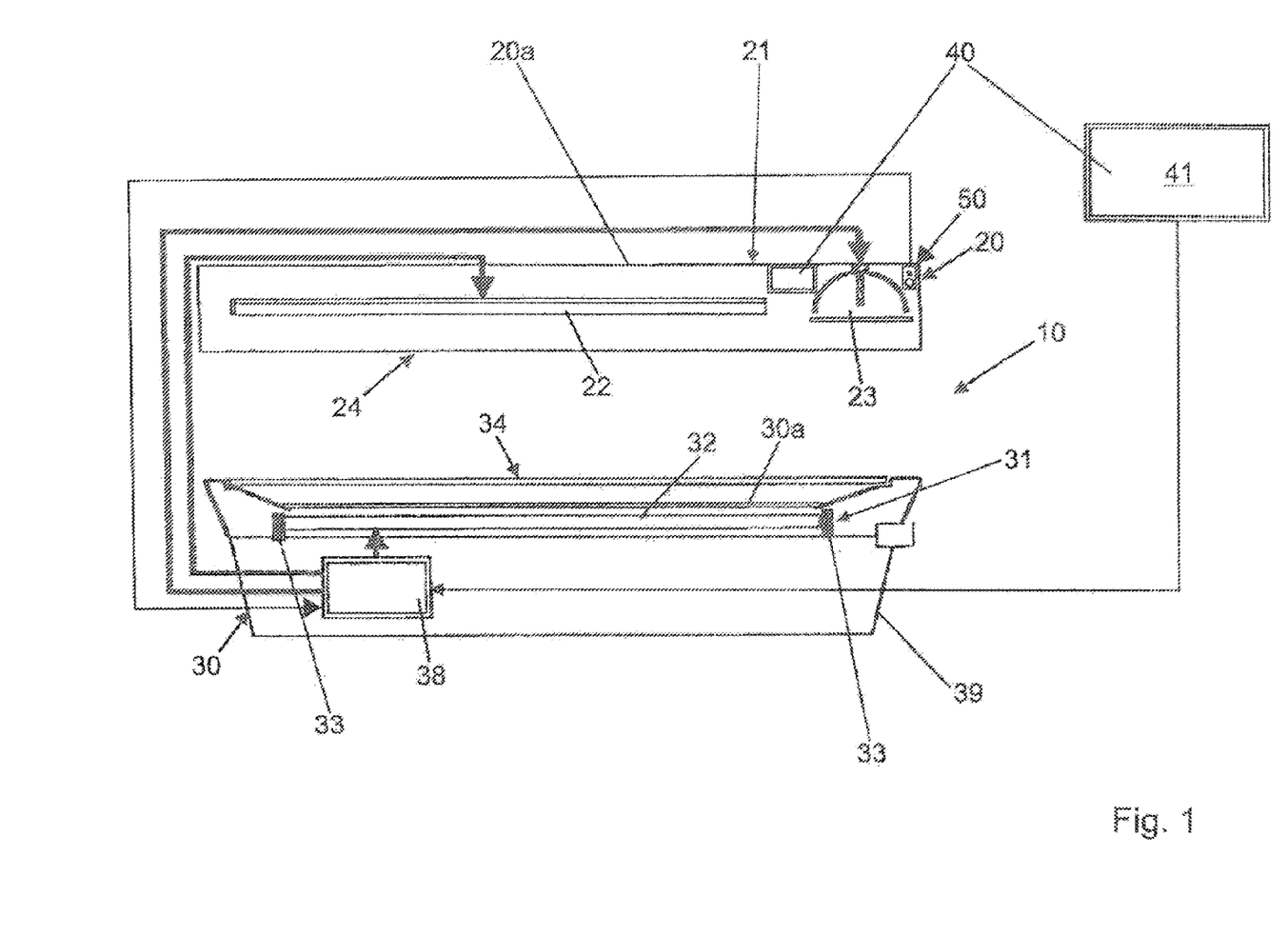
FIG. 1 shows a schematic side view of a preferred exemplary embodiment of a device according to the invention.

FIG. 1 shows a skin irradiation device 10 designed as a tanning device, which acts by means of medical-cosmetic radiation on at least the skin and partially the parts of the body lying underneath. The device 10 comprises a movable upper part 20 and a stationary lower part 30. The upper part 20 can be pivoted downward via a hinge (not shown in detail) along a linkage axis A, so that a comparatively small space in the form of a tube is provided for a recumbent person to be irradiated, the user.

Figure 2:
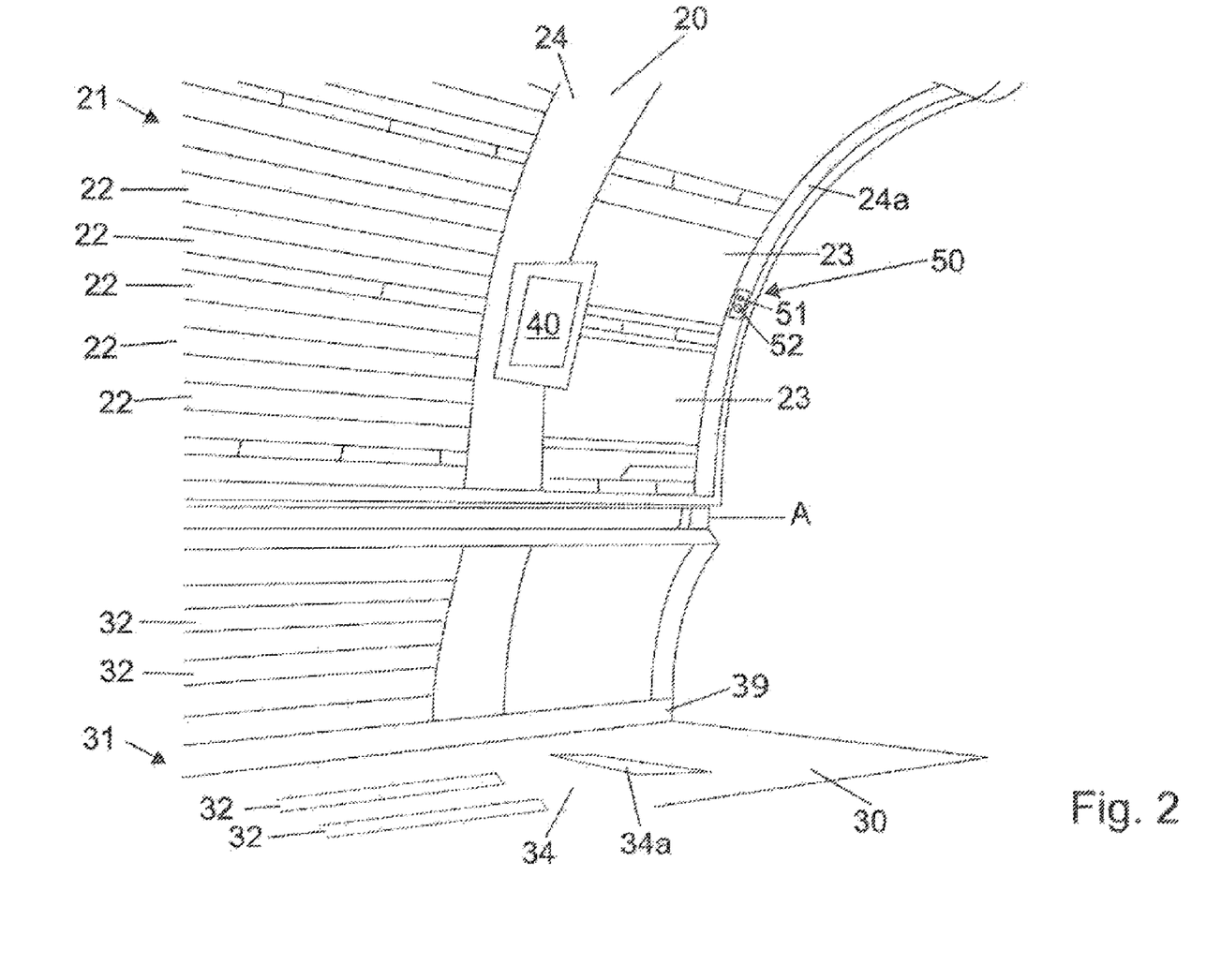
FIG. 2 shows a perspective view of the device from FIG. 1

The upper part 20 comprises an assembly 21 emitting medical-cosmetic radiation having a plurality of radiant tubes 22 emitting UV radiation, which are installed in a horizontal direction, and a further radiation device 23 designed as a face tanner based on LEDs emitting UV radiation. The upper part 20 is arranged in a housing part 24, wherein the housing 24 is formed at least in sections from polymethyl methacrylate or acrylic glass transparent for UV radiation. The wall thickness of the polymethyl methacrylate is dimensioned quite thin, since it does not have to absorb any significant mechanical loads. Furthermore, a touch display 40 is housed in the upper part 20, wherein the touch display faces toward the lower part 30 with its operating interface 41. It is possible to open an outer cover 20a of the upper part 20 to obtain access to the fluorescent tubes 22.

The lower part 30 comprises a housing part 39, which is designed like a pedestal and in which a controller 38, the electrical supply, and further parts of the skin irradiation device 10 such as fans, contactors, etc. are housed. The housing 39 furthermore comprises an assembly 31 emitting medical-cosmetic radiation, having a plurality of fluorescent tubes 32 emitting UV radiation and electronic ballast devices 33 connected at the ends to each of the fluorescent tubes 32.

A cover 30a made of polymethyl methacrylate, which covers the assembly 31, is provided above the assembly 31 emitting UV rays and above the radiant tubes 32. A cover 34, which has an upper finishing surface facing toward the upper part 20, is provided above the cover 30a. A neck support 34a on the finishing surface 34 centers the head of the user, so that the face tanners 23 face toward the face of the user, and the radiant tubes 22, 32 face toward the torso of the user. The mouth of the user is also defined quite precisely in its position in this way.

If a person to be irradiated now lies down on the finishing surface 34, this person can control the power of the assemblies 21, 31, 23 emitting UV radiation, for example, starting from a preset standard value, via the controller 38, and can do so in each case independently of one another. If the person to be irradiated wishes to change the power of the assemblies 21 and/or 31 emitting UV radiation, he can input corresponding commands via a menu in the touch display 40, which is connected to the controller 38. The touch display 40 can then be permanently installed in the skin irradiation device 10, in particular in the region of the upper part 20 facing toward the face of the person to be irradiated. It is also possible to play back music or the like via loudspeakers installed in the upper part 20.

However, in the case of the input of commands via the touch display 40, the circumstance is problematic that in principle this has to take place before the action of the UV radiation on the body of the user. This is because as soon the assemblies 21, 31, 23 emitting UV radiation are switched on, the user has to keep his eyes closed and depending on the applicable regulation even has to wear protective glasses. However, the touch display 40 may not be reliably read through the protective glasses. Therefore, an acoustic operating unit 50 is additionally formed in the upper housing part 24, which consists of a microphone 51 and a button 52 designed as a pushbutton.

The acoustic operating unit 50 is arranged for this purpose at one axial end of the movable upper housing part 24, specifically approximately at the highest point of the tube formed when the upper housing part 24 is pivoted down. At the same time, the acoustic operating unit 50 is arranged at a proximal end of the upper housing part 24, in which a frame section 24a reinforcing the housing part 24 is also formed. The microphone 51 is therefore located outside the direct radiation of the radiation device 23, so that it is not heated up in a harmful matter. To be able to capture the soundwaves of the user, the acrylic glass material of the upper housing part 24 is penetrated by a cylindrical drilled hole, into which the microphone 51 is inserted.

The controller 38 comprises an evaluation unit having a memory in which speech inputs are stored, wherein the evaluation unit is capable by means of software of comparing speech inputs of the user for correspondence with stored commands. If a threshold value of the correspondence with a stored control command is exceeded, the speech input is assigned as relating to this control demand and the controller 38 causes a corresponding control command to be output to the means for acting 22, 32, 23. In addition to the means for acting by medical-cosmetic radiation, further means for acting also come into consideration, for example, a circulating body ventilation, a face ventilation, the moisture proportion in the ventilation, and more. In addition, further operating parameters can also be set, for example, the volume of the music, the music program, and more.

The evaluation unit is optionally activated by stating a keyword, for example a name of the device, for example "Eve", by pressing the button 52, or by touching the display 40, i.e., the commands subsequently stated are compared for correspondence with permissible control commands. As long as the evaluation unit is ready to receive speech inputs, operating parameters causing noises are reduced, for example music playback, circulating body ventilation, and the like.

The speech input comprises in this case an operating parameter, for example, face lamps, body lamps, LEDs, body ventilation, face ventilation, temperature, moisture feed, music playback, volume, aroma feed, red light, blue light, waterjet strength, massage intensity, massage program, light program. In addition to the operating parameter, a set of parameter variables is predefined which characterize the operating parameter. The parameter variable reads, for example, "plus" for incrementing the operating parameter, "minus" for decrementing the operating parameter, "maximum" for setting the maximum value of the operating parameter, "minimum" for setting the minimum value of the operating parameter, "standard" for setting a moderate value of the operating parameter, "on" for switching the operating parameter on, and "off" for switching the operating parameter off.

For example, if the user says "Eve face lamps maximum", the evaluation unit recognizes due to the keyword "Eve" that it is activated and that the following speech inputs are commands. If the words "face lamps maximum" are then correctly recognized, the controller 38 prompts the face lamps 23 to act with maximum set power on the user.

As soon as the keyword is recognized, the evaluation unit prompts the controller 38 to reduce the operating parameters linked to a noise development, so that the microphone 51 is not interfered with by the noises when detecting the speech input. The evaluation unit acknowledges the successfully identified speech input by an acoustic signal which signals that the speech command was understood.

By way of the speech input, it is possible to adjust the device 10 to the requirements of the user without the use of the eyes even in running operation. In particular, it is not necessary to switch off the assemblies for acting with UV light during the change of the parameters.

The invention has been described above on the basis of an exemplary embodiment in which the device is designed like a tanning bed. It is obvious that the communication with speech in the described manner can also be provided in other devices for acting on parts of a body, for example in wellness devices, in particular in massage beds The invention has been described above on the basis of an exemplary embodiment in which the medical-cosmetic radiation essentially comprises UV radiation of the ranges UV A and UV B. It is obvious that radiation of the further medical-cosmetic radiation spectra can also be used for irradiating the skin or regions lying below the skin.

The invention has been described above on the basis of an exemplary embodiment in which the medical-cosmetic radiation is UV radiation generated by using radiant tubes 22, 32. It is obvious that UV radiation especially and medical-cosmetic radiation in general can also be generated in ways other than the use of radiant tubes, for example by LEDs or halogen lamps.

The invention has been described above on the basis of an exemplary embodiment, in which the device 10 is formed having a horizontally aligned lower part 30 having a recumbent surface 34 and an upper part 20 that can be pivoted down. It is obvious that the device can also be designed as a vertical sun bed in which the housing parts in which the means for acting are housed are set up vertically and in which the pivotable housing part is provided like a door for the access into the interior designed in the form of a vertical tube or a vertical tunnel. The microphone is expediently arranged in this case on the stationary housing part, preferably in a region above the section of the housing which faces toward the user during the action.

The invention claimed is:

1. A device for acting on at least parts of the body of a user, in particular with medical-cosmetic radiation and/or by mechanical influencing, comprising
    means for acting on the human body, which comprise adjustable operating parameters, and
    a controller connected to the means for acting, which sets the operating parameters,
    wherein at least one microphone is provided, by which speech inputs of the user for controlling the operating parameters can be captured, and
    in that the microphone is connected to an evaluation unit through a first input, the evaluation unit being configured to convert speech inputs captured by the microphone into control commands for the means for acting, wherein the evaluation unit comprises:
    a memory unit having the control commands stored therein,
    a software program stored in the memory unit as a set of instructions for execution by the evaluation unit, the software program being programmed to:
    activate the evaluation unit upon speech input of a key word,
    as soon as the evaluation unit is activated by the key word, prompt the controller to reduce operating parameters linked to a volume development and operating parameters linked to a noise development, so that the microphone is not interfered with by noises when detecting a following next speech input, and reverse the reducing a pre-settable time after an end of the speech input,
    compare a following next speech input for correspondence with a stored control command and obtain a value of the correspondence from the comparison, and
    if the value of the correspondence exceeds a predetermined threshold value of the correspondence associated with the control command, then the controller outputs the control command to the means for acting.

2. The device of claim 1, wherein a loudspeaker is provided, and in that the evaluation unit confirms successfully recognized speech inputs with an acoustic signal.

3. The device of claim 1, wherein the evaluation unit is activatable by speech input of a keyword.

4. The device as claimed in claim 1, wherein the evaluation unit is activatable by touching a touch-sensitive display screen (40).

5. The device of claim 1, wherein a button is provided next to the microphone, and in that the evaluation unit is activatable by actuating the button.

6. The device of claim 1, wherein a display and a loudspeaker are provided, and in that optical and/or acoustic explanations of the speech commands are displayable via the display and the loudspeaker.

7. The device of claim 1, wherein the operating parameters are selected from the group comprising face lamps, body lamps, LEDs, body ventilation, face ventilation, temperature, moisture feed, music playback, volume, aroma feed, red light, blue light, waterjet strength, massage intensity, massage program, light program.

8. The device of claim 1, wherein, in addition to the designation of the operating parameter, a parameter variable is predefinable which is selected from the group comprising plus, minus, maximum, minimum, standard, on, off.

9. The device of claim 1, wherein the body parts are selected from the group comprising the skin, the connective tissue, the musculature, the bones.

10. The device of claim 1, wherein speech parameters of the user are stored on a memory unit and after reading in the data are usable for setting the evaluation unit.

11. The device of claim 1, wherein the controller also sets means other than the means for acting on the human body.

12. The device of claim 1, wherein the device is designed as a hydromassage device with a membrane-like recumbent surface for the user, comprising at least one activatable massage nozzle underneath the recumbent surface, which can direct a massage waterjet against the membrane-like recumbent surface to massage the user lying thereon.

13. The device of claim 1, wherein the means for acting are selected from the group comprising fluorescent tubes emitting UV light, fluorescent tubes emitting visible light, LEDs emitting UV light, LEDs emitting visible light, high-pressure lamps emitting UV light.

14. The device of claim 1, wherein a portable mobile terminal having a microphone is connectable to the device, and in that the microphone of the mobile device captures the speech inputs of the user.

15. The device of claim 1, wherein the means for acting are housed in a self-supporting housing, on which the microphone is arranged.

16. A device for acting on at least parts of a body of a user with medical-cosmetic radiation, comprising
- a self-supporting housing, in which an assembly emitting medical-cosmetic radiation for acting on the human body with adjustable operating parameters is housed and
- a controller connected to the assembly for acting, which sets the operating parameters,
- wherein at least one microphone is provided on the housing, by which speech inputs of the user for controlling the operating parameters can be captured, and
- the microphone is connected to an evaluation unit through a first input, the evaluation unit being configured to convert the speech inputs captured by the microphone into control commands for the assembly for acting, the evaluation unit comprising:
  - a memory unit having the control commands stored therein,
  - a software program stored in the memory unit as a set of instructions for execution by the evaluation unit, the software program being programmed to:
    - activate the evaluation unit upon speech input of a key word,
    - as soon as the evaluation unit is activated by the key word, prompt the controller to reduce operating parameters linked to a volume development and operating parameters linked to a noise development, so that the microphone is not interfered with by noises when detecting a following next speech input, and reverse the reducing a pre-settable time after an end of the speech input,
    - compare a following next speech input for correspondence with a stored control command and obtain a value of the correspondence,
    - if the value of the correspondence exceeds a predetermined threshold value of the correspondence associated with the control command, then the controller outputs the control command to the means for acting.

17. The device of claim 16, wherein the housing comprises a stationary housing part and a movable housing part, wherein the movable housing part is coupled via a linkage axis (A) with the stationary housing part.

18. The device of claim 17, wherein the stationary housing part forms a recumbent surface for the user, and in that the movable housing part is pivotable down to the stationary housing part to form a tube.

19. The device of claim 17, wherein the microphone is arranged on the movable housing part.

20. The device of claim 19, wherein the microphone is arranged at an axial end of the movable housing part.

21. The device of claim 17, wherein the microphone is arranged in a drilled hole of a stable plastic shell forming the movable housing part and at least predominantly transparent to medical-cosmetic radiation.

22. The device of claim 17, wherein the microphone is arranged outside the region of direct irradiation with medical-cosmetic radiation.

23. The device of claim 17, wherein the microphone is arranged in the region of a frame section reinforcing the housing part.

24. A method for acting on at least parts of a body of a user, in particular with medical-cosmetic radiation and/or by mechanical influencing, the method comprising
- providing means for acting on the human body, which comprise adjustable operating parameters,
- providing a controller connected to the means for acting, which sets the operating parameters, wherein the user specifies at least some of the operating parameters by speech input, and in that the speech inputs captured by at least one microphone are convertable by an evaluation unit into control commands for the means for acting,
- activating the evaluation unit upon speech input of a key word,
- as soon as the evaluation unit is activated by the key word, prompting the controller to reduce operating parameters linked to a volume development and operating parameters linked to a noise development, so that the microphone is not interfered with by noises when detecting a following next speech input, and reverse the reducing a pre-settable time after an end of the speech input,
- comparing a following next speech input for correspondence with a stored control command and obtaining a value of the correspondence, and
- if the value of the correspondence exceeds a predetermined threshold value of the correspondence associated with the control command, outputting the control command, via the controller, to the means for acting.

25. The method of claim 24, wherein the operating parameters stored in the evaluation unit are selected from the group comprising face lamps, body lamps, LEDs, body ventilation, face ventilation, temperature, moisture feed, music playback, volume, aroma feed, red light, blue light, waterjet strength, massage intensity, massage program, light program.

26. The method of claim 25, wherein parameter variables are stored in the evaluation unit for the stored operating parameters, which are selected from the group comprising plus, minus, maximum, minimum, standard, on, off.

27. The device of claim 1, wherein the software program is further programmed to:
- if the value of the correspondence does not exceed the predetermined threshold value of the correspondence associated with the control command, then prompt questions, via a loudspeaker of the device, to the user to further clarify the speech input.

28. The device of claim 1, comprising:
- a loudspeaker for providing acoustic signals to the user, the loudspeaker connected to the evaluation unit through a second input that is separate from the first input that connects the microphone to the evaluation unit, the second input configured to transmit the acoustic signals to the evaluation unit; and
- wherein the acoustic signals are inverted by the evaluation unit after entering the second input, so that the acoustic signals captured randomly by the microphone are expressly not understood as a control command.

* * * * *